US00PP23797P3

(12) United States Plant Patent
Maillard et al.

(10) Patent No.: US PP23,797 P3
(45) Date of Patent: Aug. 6, 2013

(54) SWEET CHERRY TREE NAMED 'ROSILAM'

(50) Latin Name: ***Prunus avium* (L.) L.**
Varietal Denomination: ROSILAM

(75) Inventors: Arsene Maillard, Elne (FR); Laurence Maillard, Elne (FR)

(73) Assignee: Agro Selections Fruits, Elne (FR)

( * ) Notice: Subject to any disclaimer, the term of this patent is extended or adjusted under 35 U.S.C. 154(b) by 365 days.

(21) Appl. No.: 13/064,028

(22) Filed: Mar. 2, 2011

(65) Prior Publication Data

US 2011/0219481 P1 Sep. 8, 2011

(30) Foreign Application Priority Data

Mar. 2, 2010 (QZ) ..... PBR 20100512

(51) Int. Cl.
*A01H 5/00* (2006.01)

(52) U.S. Cl.
USPC ..... Plt./181

(58) Field of Classification Search
USPC ..... Plt./181
See application file for complete search history.

(56) References Cited

U.S. PATENT DOCUMENTS

PP10,578 P * 9/1998 Hurlbut ..... Plt./181

OTHER PUBLICATIONS

PLUTO UPOV Citations for 'ROSILAM'.*

* cited by examiner

*Primary Examiner* — Wendy C Haas
(74) *Attorney, Agent, or Firm* — Westerman, Hattori, Daniels & Adrian, LLP

(57) ABSTRACT

A new and distinct variety of sweet cherry tree. The following features of the tree and its fruit are characterized with the heavy and regular production of large size fruit, with very good flavor and eating quality, with an attractive pink red skin color and with good handling and storage quality.

3 Drawing Sheets

Latin name of the genus and species of the plant claimed: *Prunus avium* (L.) L.

Variety denomination: 'ROSILAM'.

This application claims priority of Community plant variety right No. 2010/0512 filed on Mar. 2, 2010 which is hereby incorporated by reference in its entirety.

BACKGROUND OF THE NEW VARIETY

Field of the Invention

In the field of plant genetics, we conduct an extensive and continuing plant-breeding program including the organization and reproduction of orchard trees, among which peaches, nectarines, apricots, and cherries are exemplary. It was against this background of our activities that the present variety of sweet cherry tree was originated and reproduced by us in our experimental orchard located near Elne, Pyrénées Orientales, France.

ORIGIN OF THE VARIETY

The present new variety of sweet cherry tree (*Prunus avium* L.) was developed by us in our experimental orchard located in France. 'ROSILAM' sweet cherry tree originated in a cultivated area of the South of France, in the Pyrénées-Orientales department where it was also tested. This zone also called Roussillon is subject to a Mediterranean climate. The winter is generally sweet and the summer is hot and dry. The total amount of cold hours lower than 7° C. (Celsius) varies from 600 hours to 1200 hours. The total amount of sunshine hours is an average of 2400 hours to 2800 hours per year.

The 'ROSILAM' variety results from a controlled cross between 'BIGALISE® ENJIDEL' (non-patented) and 'RAINIER' (non-patented). 'BIGALISE® ENJIDEL' is characterized by a good productivity but a slow maturity of fruit. Fruit is of large size, very firm, with a sweet flavor, low acidity, and a shiny red color. The blooming period is late March. The maturity period is semi-early, generally form end of May to beginning of June in the South of France. RAINIER is a bicolour cherry, round and reniform, with a yellow orange red skin color and a creamy white flesh. Fruit is of very good gustative quality. The blooming period begins generally around the $20^{th}$ of March. The maturity period is around the $10^{th}$ of June in the South of France. It was obtained by hybridizing and propagated by grafting. It has been determined to have unique tree and fruit characteristics making it worthy for commercial fresh fruit production. There are no known effects of this standard rootstock on this scion cultivar. Asexually propagated plants remained true to the original tree and all characteristics of the tree and the fruit were transmitted. The plant was reproduced asexually in Elne, Pyrénées-Orientales department, France.

SUMMARY OF THE NEW VARIETY

The present new and distinct variety of sweet cherry tree produces large fruits with very good flavor, firmness and eating quality. The fruit is further characterized its attractive pink red skin color and maturing in the medium early season in France (near the $10^{th}$ of June).

BRIEF DESCRIPTION OF THE DRAWINGS

The accompanying photographs show typical specimens of the new variety as depicted in color as nearly true as is reasonably possible in color illustrations of this character. These specimens were obtained at the Elne Experiment Station, South of France.

BOTANICAL DESCRIPTION OF THE VARIETY

Figure 1:
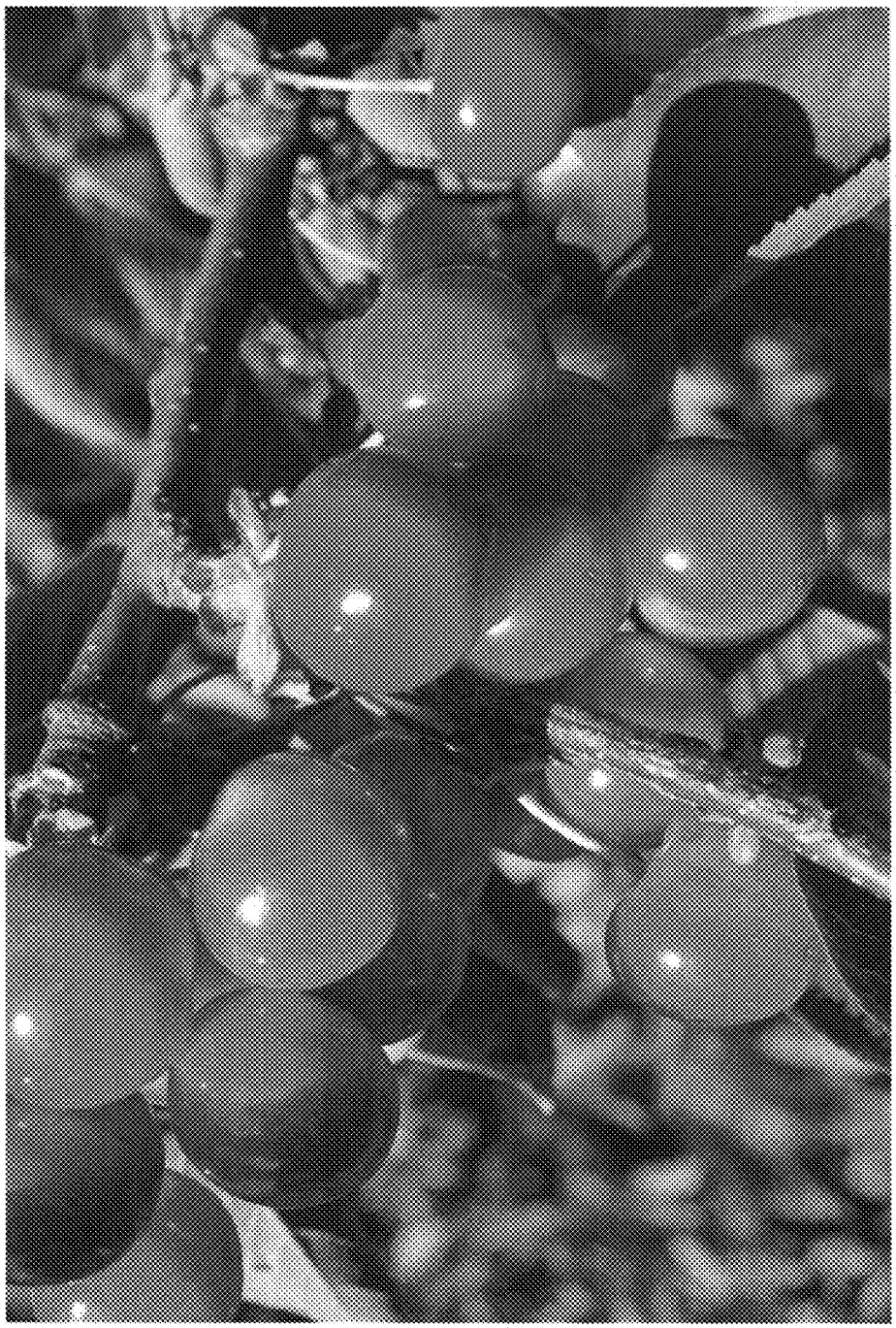
FIG. 1 shows a front view of a fruit clustering of 'ROSILAM' variety.
Figure 2:
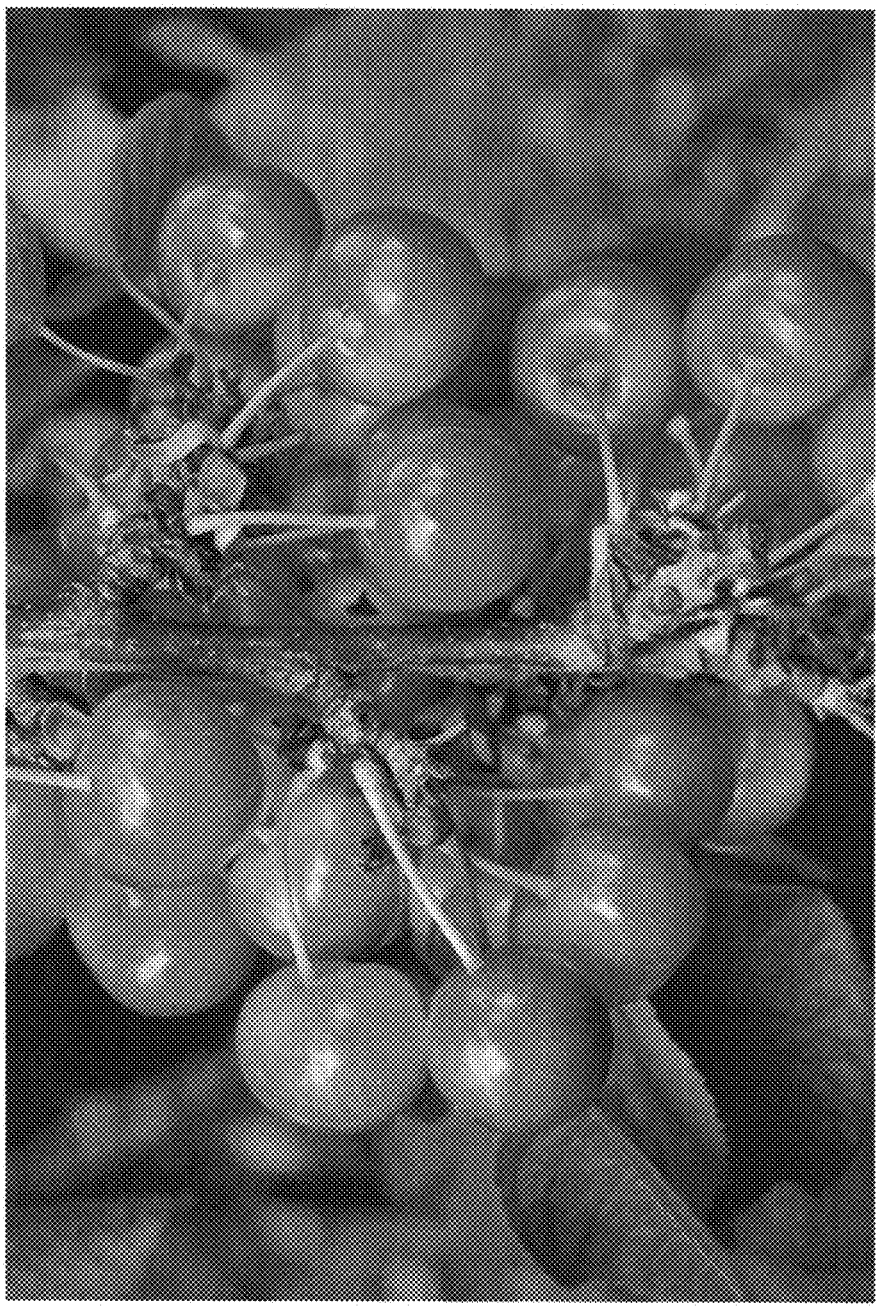
FIG. 2 shows an upper view of a fruit clustering of 'ROSILAM' variety.
Figure 3:
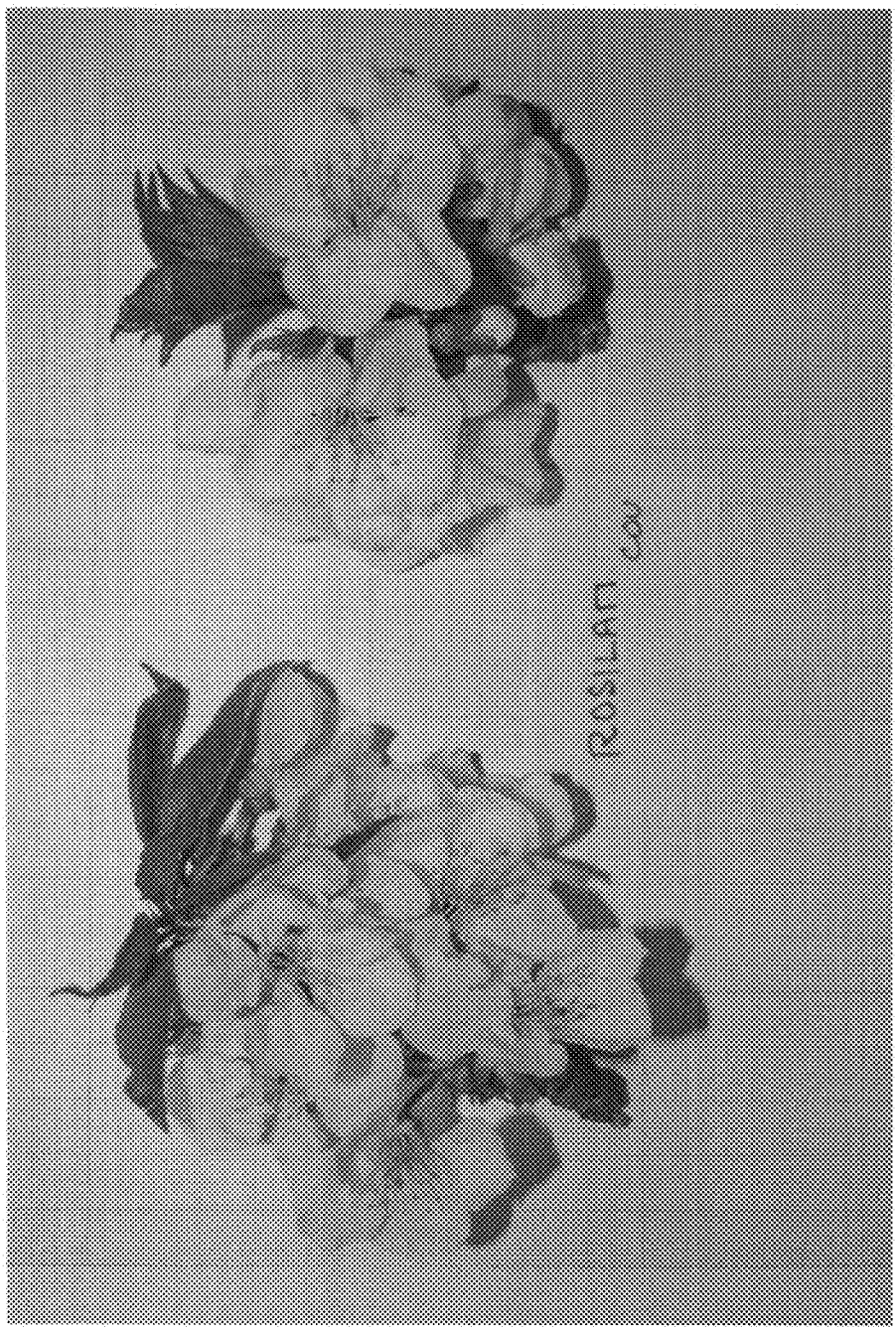
FIG. 3 shows typical white flowers of 'ROSILAM' variety at blooming with some leaves.

The following is a detailed botanical description of the new variety of sweet cherry tree, its flowers, foliage and fruit, as based on observations of specimens grown near Elne, South of France, with color in accordance with The R.H.S. Color Chart (Fourth Edition) provided by The Royal Horticultural Society of Great Britain.

The main characteristics of this new variety of sweet cherry are a large fruit size with a color of skin from yellow with blush to orange red. The fruit flesh is pink on cream. The fruit is very firm.

The time of beginning of flowering is early and the time of beginning of fruit ripening is medium.

In comparison with the parent cherry tree 'RAINIER' the present variety has a fruit flesh more pink red and of a larger size. The fruit is firmer than RAINIER fruit. The fruit flavor is sweeter and less astringent. The flowering period is earlier from seven days and begins on the second two-weeks of March. The maturity period is earlier of 10 days and begins around end of May.

Concerning the resistance to pests and diseases 'ROSILAM' is medium sensitive to *Monilia*.

DETAILED DESCRIPTION

Referring more specifically to the pomological details of this new and distinct variety of sweet cherry tree, the following has been observed under the ecological conditions prevailing at the orchards located near the town of Elne, Pyrénées-Orientales department, France.

All observations have been done on rootstock cultivar. The rootstock was a "MAXMA 14" tree. The first year the cherry tree is generally cut at 2.50 meters height. The length in one year for each lateral shoot varies from 0.60 meters to 0.80 meters. We are cutting the cherry trees during the second year to a height of 2.50 meters. The form of the cheery trees is cylindrical and the diameter is limited to 2 meters.

All major color code designations are by reference to The R.H.S. Color Chart (Fourth Edition) provided by The Royal Horticultural Society of Great Britain.

Tree:

*Size.*—Medium to high as compared to other commercial sweet cherry cultivars. The tree size the first year was approximately 2.50 meters. The tree was pruned during each following dormant season to a height of approximately 2.50 meters. Current seasons shoots growth could reach 0.80 meters. So the tree size from the second year (second and next years) reached a final height of 3.30 meters with current seasons shoots length comprised.

*Spread.*—Approximately 1.0 meter. The whole orchard was oriented to a central leader organization, with tree lines spaced of 4.0 meters and trees spaced of 1 meter in a same tree line.

*Vigor.*—Medium, tree growth reaching 0.60 to 0.80 meters the first growing season.

*Productivity.*—Good to very good productivity. The new variety produces adequate fruit set annually on a regular basis. The number of the fruit set varies with the prevailing climatic conditions and cultivar practices employed during the bloom period, and is therefore not distinctive of the present variety.

*Bearer.*—Very regular and quantitative. The extinction of the clusters of May improves the calibre and firmness of the fruit.

*Form.*—Naturally spreading to semi-upright.

*Hardiness.*—Hardy in all stone fruit growing areas of France and especially where the chilling requirement is between 350 and 1200 hours. No injury with a temperatures as low as −12° C. in winter. Good resistance to late frosts.

Trunk:

*Size.*—Medium. Measured between 5.5 centimeters and 7.0 centimeters above 30.0 centimeters from ground, on 3$^{rd}$ growing season.

*Bark texture.*—Rough with lenticels.

*Lenticels.*—High number of lenticels. At the 3$^{rd}$ growing season, lenticels are 0.2 to 0.3 centimeters in height and 0.4 to 0.8 centimeters in width.

*Lenticels color.*—Color of lenticels is RHS GREYED GREEN 197 A-C.

*Bark color.*—Grey and silver brown (from RHS 166 A to RHS 200 B) with grey zones (RHS GREY 201 C-D).

Branches:

*Size.*—Medium to large for the new growth. Medium to large for the branches at the 3$^{rd}$ growing season.

*Diameter.*—Average diameter of 14.0 to 23.0 millimeters.

*Surface texture.*—Smooth. Wood that is several years old has no furrowed appearance.

*Color.*—Old growth is brown (RHS BROWN 200 B-C with zones of RHS BROWN 201 B-C).

Current season shoots:

*Diameter.*—Average diameter from 6.0 to 10.0 millimeters.

*Surface texture.*—Smooth. Wood that is several years old has no furrowed appearance.

*Crotch angles.*—Primary branches are considered variable, but the crotch angles are generally between 60 degrees and 70 degrees from the horizontal axis. This particular characteristic is not considered distinctive of the variety, however.

*Internode.*—Generally from 25.0 millimeters to 40.0 millimeters length.

*Color.*—New growth is more orange brown more or less dark (RHS GREYED ORANGE 176 B-C-D).

Leaves:

*Size.*—Large for the species. Leaf measurements have been taken from vigorous, upright, current-season growth at approximately mid-shoot. The ratio leaf length/leaf width is above 2.03.

*Length.*—From 167.0 to 186.0 millimeters with leaf petiole. Average length with petiole 182.0 millimeters.

*Width.*—From 86.0 to 97.0 millimeters. Average width 89.0 millimeters.

*Leaf base shape.*—Elongated relative to the leaf longitudinal axis.

*Leaf form.*—Elliptic, round base.

*Apex.*—Acuminate.

*Base.*—Cuneate.

Leaf color:

*Upper leaf surface.*—Dark green (RHS YELLOW GREEN 137 A).

*Lower surface.*—A lighter green than the upper leaf surface (RHS GREEN 137 B-C).

*Leaf texture.*—Smooth and glabrous. The lower surface is also smooth.

*Leaf venation.*—Pinnately veined.

Mid-vein:

*Color.*—Light green with a yellow touch (RHS YELLOW GREEN 145 C-D) and evolves with maturity.

*Leaf margins.*—Slightly undulating.

*Form.*—Considered slightly dentate.

*Uniformity.*—Leaves are isolated.

Leaf petioles:

*Size.*—Considered medium to long.

*Length.*—About 35.0 to 47.0 millimeters. Average length 35.0 millimeters.

*Diameter.*—About 2.5 to 3.0 millimeters.

*Color.*—Upper surface pale red (varies from RHS GREYED PURPLE 183 D to 184 D). Lower surface light green (RHS YELLOW GREEN 145 A-C).

Leaf glands:

*Size.*—Considered small to medium. Their length is about 2.0 millimeter.

*Number.*—Generally 2 and sometimes 3.

*Type.*—Reniform.

*Color.*—Purple green (RHS GREYED PURPLE GROUP 185 A-B).

Leaf stipules:

*Generally.*—No leaf stipules were observed.

Flowers:

Flower buds:

*Generally.*—At pre-floral stage of development, the floral buds have a conic shape with a round tip. Their form is evolving until blooming, with variables dimensions. Just before blooming, floral buds are approximately 12.0 millimeters wide and approximately 20.0 millimeters long.

*Color.*—This characteristic is dependent upon the proximity to bloom. At pre-floral stage of development, the bottom of the flowers buds, or calyx formed by sepals, is of green color (RHS GREEN 138 A-C to RHS YELLOW GREEN 145 A-B); the corolla formed by petals, is generally white (RHS WHITE 155 C).

*Hardiness.*—The buds are considered hardy under typical central Pyrénées-Orientales department climatic conditions. No winter injury was noted during the last several years of evaluation in the central Pyrénées-Orientales department, with winter temperatures as low as −10° C. in January. The current variety has not been intentionally subjected to drought or heat stress, but the variety showed a very good resistance in orchard to temperatures up to 42° C. with an average temperature between 28° C. and 30° C. during 3 weeks in summer.

*Date of bloom.*—Generally late March. The first bloom was observed on Apr. 3, 2003. Second to fifth blooms took place respectively on Mar. 12, 2007, Mar. 11, 2008, Mar. 19, 2009, and Apr. 1, 2010 (exceptionally late due to winter climatic conditions in March 2010).

*Blooming time.*—Considered semi-early in relative comparison to other commercial cherry cultivars grown in the Pyrénées-Orientales department, France. The date of full bloom is observed at the middle of the blooming period. The date of bloom varies slightly with climatic conditions and cultural practices.

*Blooming period.*—Average 12 days. This characteristic varies slightly with the prevailing climatic conditions.

*Flower type.*—The variety is considered to have a showy type flower.

*Flower size.*—Considered large. Average diameter 40.0 millimeters when totally opened.

*Bloom quantity.*—Considered abundant, approximately 60 flowers per meter.

*Flower bud frequency.*—Generally 4 to 8 flower buds appear per node.

Petal:

*Size.*—Considered as large for the species.

*Length.*—Generally about 19.0 millimeters.

*Width.*—Generally about 19.0 millimeters.

*Petal form.*—Large form, elliptic, usually no overlapping.

*Petal count.*—Nearly always 5.

*Petal texture.*—Smooth and soft.

*Petal color.*—White color (RHS WHITE 155C) on both surfaces.

*Fragrance.*—Soft.

Petal claw:

*Form.*—The claw is considered to have a conic form with a slightly rounded tip.

*Length.*—Approximately 7.0 millimeters.

*Width.*—Approximately 4.5 millimeters.

*Petal margins.*—Smooth.

Petal apex:

*Generally.*—The petal apices are generally complete at the tip and round.

Flower pedicel:

*Length.*—Considered medium to long and having an average length of approximately 15.0 to 17.0 millimeters.

*Diameter.*—Average 1.5 millimeters.

*Color.*—Green (RHS GREEN 143 C-D).

Calyx:

*Internal surface texture.*—Smooth and glabrous.

*Color.*—The inner surface is washed-yellow green (varies from RHS GREEN 138 A-C to RHS YELLOW GREEN 145 A-B) with pink purple zones (RHS GREYED RED GROUP 182 A-C). The outer surface of the calyx is considered green (RHS GREYED PURPLE 183 A-D).

Sepals:

*Surface texture.*—The outer surface has a thin texture.

*Size.*—Usually considered medium. Elliptic shape.

*Color.*—The upper surface is green (RHS varies from GREEN 138 A-C to YELLOW GREEN 145 A-B) with pink purple zones (RHS GREYED RED GROUP 182 A-C).

*Average number of stamens per flower.*—Average 32 stamens per flower.

Anthers:

*Length.*—Medium.

*Color.*—Yellow orange red color (RHS YELLOW ORANGE 16 A-B). Anthers are becoming brown (RHS GREYED RED 175 B-C) at maturity. The color evolves with flowering.

*Pollen production.*—Pollen is abundant, and has a yellow color (RHS YELLOW ORANGE 17 B-C) that varies with maturity. The present variety is auto-fertile (self-pollinating).

Filaments:

*Size.*—Variable in length, approximately 10.0 millimeters in length.

*Color.*—Considered as white (RHS WHITE 155 C).

Pistil:

*Number.*—Usually 1.

*Length.*—Approximately from 15.0 to 17.0 millimeters including the ovary.

*Color.*—Considered very pale green (RHS YELLOW GREEN 150 D to RHS YELLOW GREEN 151 D). The color is evolving with flowering.

*Surface texture.*—Glabrous.

Fruits:

*Maturity when described.*—Very firm at maturity.

*Date of first picking.*—Jun. 7, 2010, varies slightly with climatic conditions. Particularly late in 2010 because March 2010 was very cold.

*Date of last picking.*—Jun. 14, 2010, varies slightly with climatic conditions. Particularly late in 2010 because March 2010 was very cold.

*Ripening period.*—Approximately 7 to 8 days.

Size:

*Generally.*—Considered large, with a homogeneous size between them. Clusters of 1 to 3 fruits.

*Average cheek diameter.*—About 25.0 millimeters.

*Average axial diameter.*—About 28.0 millimeters.

*Typical weight.*—Generally about 11.0 grams. This characteristic is highly dependent upon the prevailing cultural practices, and therefore is not particularly distinctive of the variety.

Fruit form:

*Generally.*—Reniform and round.

*Fruit suture.*—Nearly smooth, extending from the base to the apex. No apparent callousing or stitching exists along the suture line.

Suture:

*Color.*—This has generally a color similar to the blush fruit color, pink red (RHS RED GROUP 46 A-B to RED GROUP 39 A-B) on 50% to 60% of the fruit skin on a bright golden cream ground (RHS YELLOW ORANGE 22 A to 16 A) on 40% to 50% of the fruit skin.

Ventral surface:

*Form.*—Smooth.

*Apex.*—In slight depression, very small, non prominent.

*Base.*—Semi-flared. Shallow.

*Stem cavity.*—Average depth of the stem cavity is about 4.0 millimeters. Average width is about 12.0 millimeters.

Fruit skin:

*Thickness.*—Considered smooth and thin, and tenacious to the flesh depending on stage of maturity.

*Tenacity.*—Tenacious to flesh.

*Texture.*—Smooth.

*Taste.*—Semi-sweet, sugared, aromatic.

*Tendency to crack.*—None.

Color:

*Blush color.*—This blush color is a pink red (RHS GROUP 46 A-B to RED GROUP 39 A-B). The red blush covers 50% to 60% of the fruit skin surface.

*Ground color.*—The ground color is a bright golden cream color (RHS YELLOW ORANGE 22 A to 16 A). The ground color covers 40% to 50% of the fruit skin surface.

*Fruit stem.*—Medium in length, approximately 27.0 to 34.0 millimeters.

*Diameter.*—Approximately 1.5 millimeters.

*Color.*—Light green (RHS YELLOW GREEN 145A-B).

Flesh:

*Ripens.*—Homogenous.

*Texture.*—Very crunchy, luscious, juicy.

*Fibers.*—No fibers.

*Firmness.*—Very firm.

*Aroma.*—Pronounced aroma.

*Eating quality.*—Very good, very sweet, aromatic.

*Flavor.*—Semi-sweet, very sugared, aromatic. Slow acidic level. Juicy and aromatic.

*Juice.*—Large amount, very juicy. Colorless and sometimes slightly creamy (RHS YELLOW WHITE 158 B-D).

*Brix.*—Superior to 17.0°, varies slightly with amount of fruit per tree and climatic conditions.

*Color.*—Creamy yellow (RHS YELLOW WHITE GROUP 158 B-C).

Stone:

*Type.*—Semi-Clingstone.

*Size.*—Small to medium, with a form and dimensions corresponding to the stone's dimensions.

*Length.*—Average 11.0 millimeters. A

*Width.*—Average width 10.0 millimeters.

*Diameter.*—Average diameter 8.5 millimeters.

*Form.*—Large, elliptic.

*Base.*—Generally round.

*Apex.*—Round.

Stone surface:

*Surface texture.*—Smooth.

*Ridges.*—None, smooth.

Ventral edge:

*Width.*—Very shallow.

Dorsal edge:

*Shape.*—Simple.

*Stone color.*—The color of the dry stone is yellow (RHS GREYED YELLOW 161 D).

*Tendency to split.*—None.

Kernel:

*Size.*—Small to medium.

*Length.*—About 8.0 millimeters.

*Width.*—About 6.0 millimeters.

*Thickness.*—About 5.0 millimeters.

*Form.*—Ovoid, with a sharp apex and a round base.

*Pellicle.*—Slightly pubescent.

*Color.*—The kernel skin is orange brown (RHS GREYED YELLOW 162 C) with stripes (RHS GREYED ORANGE 164 B). The almond is cream-white (RHS WHITE 155 B). The kernel and its embryo are mature at the time of fruit maturity.

Use: Dessert. Fresh products.

*Market.*—Local and long distance. On the tree fruits can stay 10 days while keeping good gustative qualities. The lifetime after picking is also good.

Keeping quality: Good, held well for 30 days in cold storage at 2° C. and maintained good appearance and eating quality.

Shipping quality: Good, showed minimal bruising or scarring during picking, packing and shipping trials.

Plant/fruit disease resistance/susceptibility: Specific tests were run with regards to *Monilia* and 'ROSILAM' seems low sensitive to *Monilia.* Moreover 'ROSILAM' is low sensitive to other observed pathologies, to rupture and to conservation pathologies. No sensitivity to *Pseudomonas Syringae* was observed.

The present new variety of cherry tree, its flowers, foliage and fruit herein described may vary in slight detail due to climate, soil conditions and cultural practices under which the variety may be grown. The present description is that of the variety grown under the ecological conditions prevailing near Elne, Pyrénées Orientales (66), France (FR).

We claim:

1. A new and distinct variety of sweet cherry tree, substantially as illustrated and described, characterized by its fruit and especially by its large size, its pink red skin color, its firmness, good flavor and eating quality; the fruit is further characterized by its good handling and storage qualities.

* * * * *